(12) United States Patent
Perez-Cruet et al.

(10) Patent No.: US 8,425,612 B2
(45) Date of Patent: Apr. 23, 2013

(54) MINIMALLY INVASIVE INTERBODY DEVICE ASSEMBLY

(75) Inventors: Miguelangelo J. Perez-Cruet, Bloomfield, MI (US); John R. Pepper, Cheshire, CT (US)

(73) Assignee: Thompson MIS, LLC, Traverse City, MI (US)

( * ) Notice: Subject to any disclaimer, the term of this patent is extended or adjusted under 35 U.S.C. 154(b) by 0 days.

(21) Appl. No.: 12/961,121

(22) Filed: Dec. 6, 2010

(65) Prior Publication Data

US 2011/0077740 A1 Mar. 31, 2011

Related U.S. Application Data

(63) Continuation of application No. 11/932,175, filed on Oct. 31, 2007, now Pat. No. 7,846,210, which is a continuation-in-part of application No. 11/623,356, filed on Jan. 16, 2007, now Pat. No. 7,824,427.

(51) Int. Cl.
*A61F 2/44* (2006.01)

(52) U.S. Cl.
USPC ............ 623/17.16; 623/17.11; 606/249; 606/86 A; 606/99

(58) Field of Classification Search .......... 606/248–249, 606/90, 99, 86 A; 623/17.11–17.16
See application file for complete search history.

(56) References Cited

U.S. PATENT DOCUMENTS

| | | | | |
|---|---|---|---|---|
| 6,290,724 | B1 * | 9/2001 | Marino | 623/17.11 |
| 2010/0036494 | A9 * | 2/2010 | Errico et al. | 623/17.11 |

* cited by examiner

*Primary Examiner* — Eduardo C Robert
*Assistant Examiner* — Christina Negrellirodriguez
(74) *Attorney, Agent, or Firm* — McAndrews Held & Malloy, Ltd.

(57) ABSTRACT

A minimally invasive interbody device assembly that includes an interbody device that restores the disc space height between two vertebrae and an instrument detachably coupled to the interbody device for positioning the device in the disc space and delivering bone material to the disc space that is distributed on both sides of the interbody device. The device is inserted into the disc space using the instrument in a direction so that the wide dimension of the device is substantially parallel to the body of the vertebrae. The device is then rotated by the instrument so that the wide dimension of the device becomes perpendicular to the vertebral body so as to cause the disc space height to be restored. Bone graft material is then forced down the instrument so that the bone graft material is distributed on both sides of the device. The instrument is then detached from the device.

22 Claims, 10 Drawing Sheets

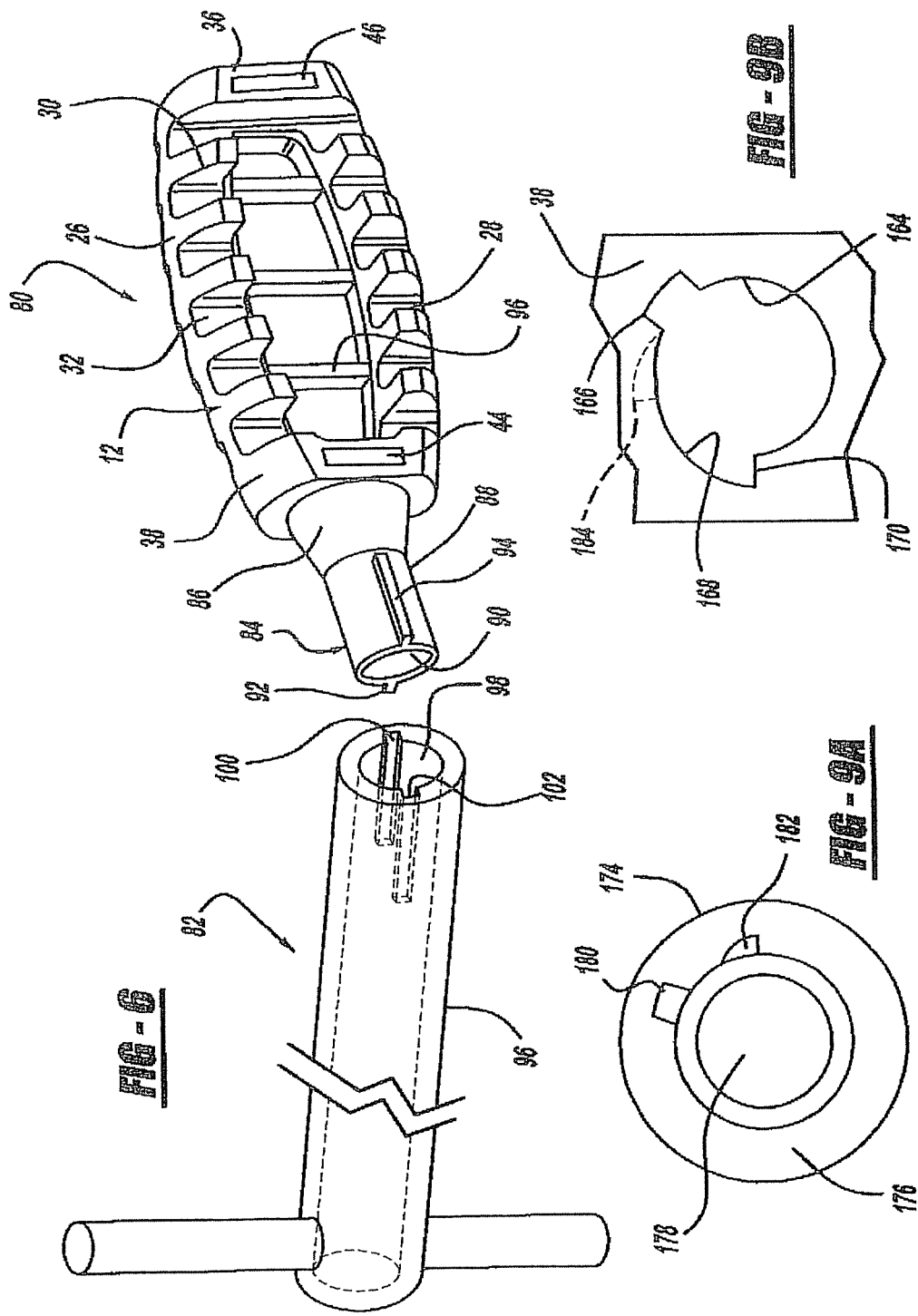

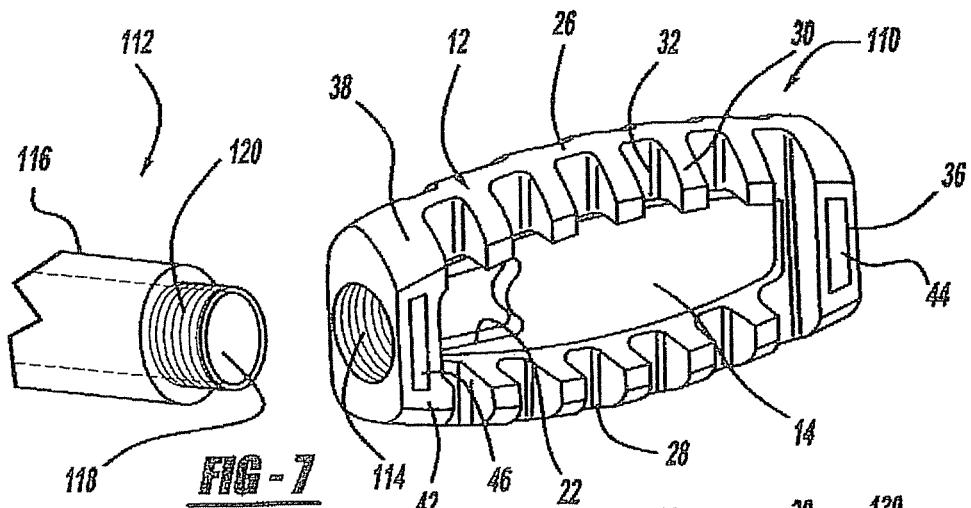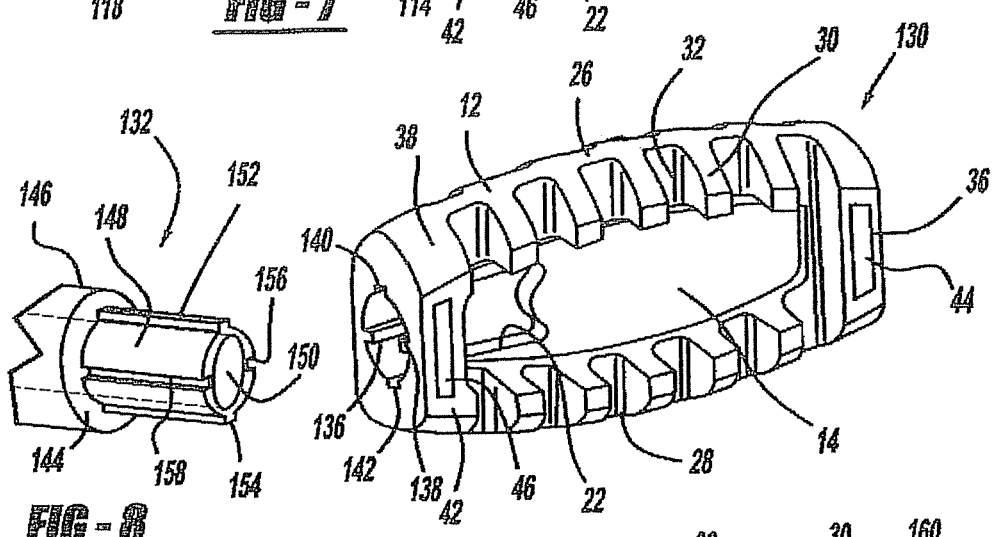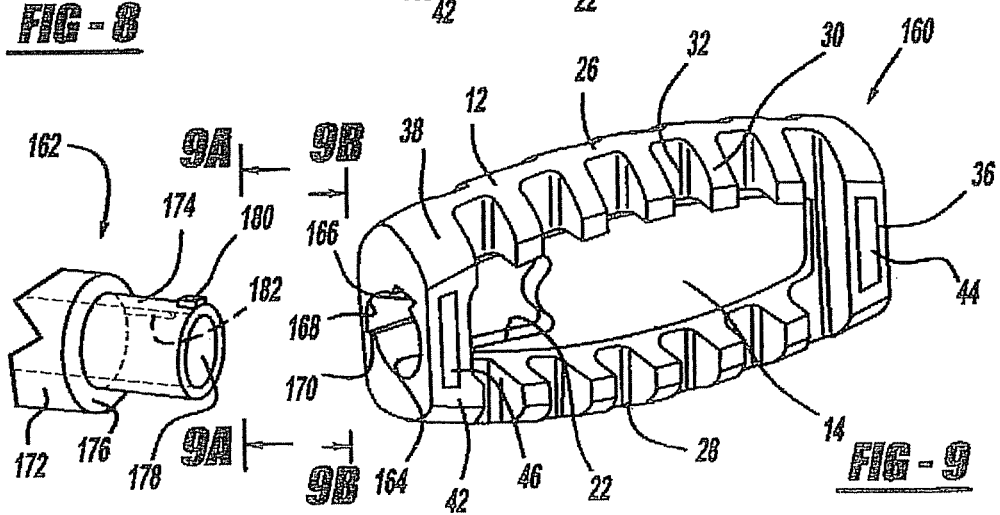

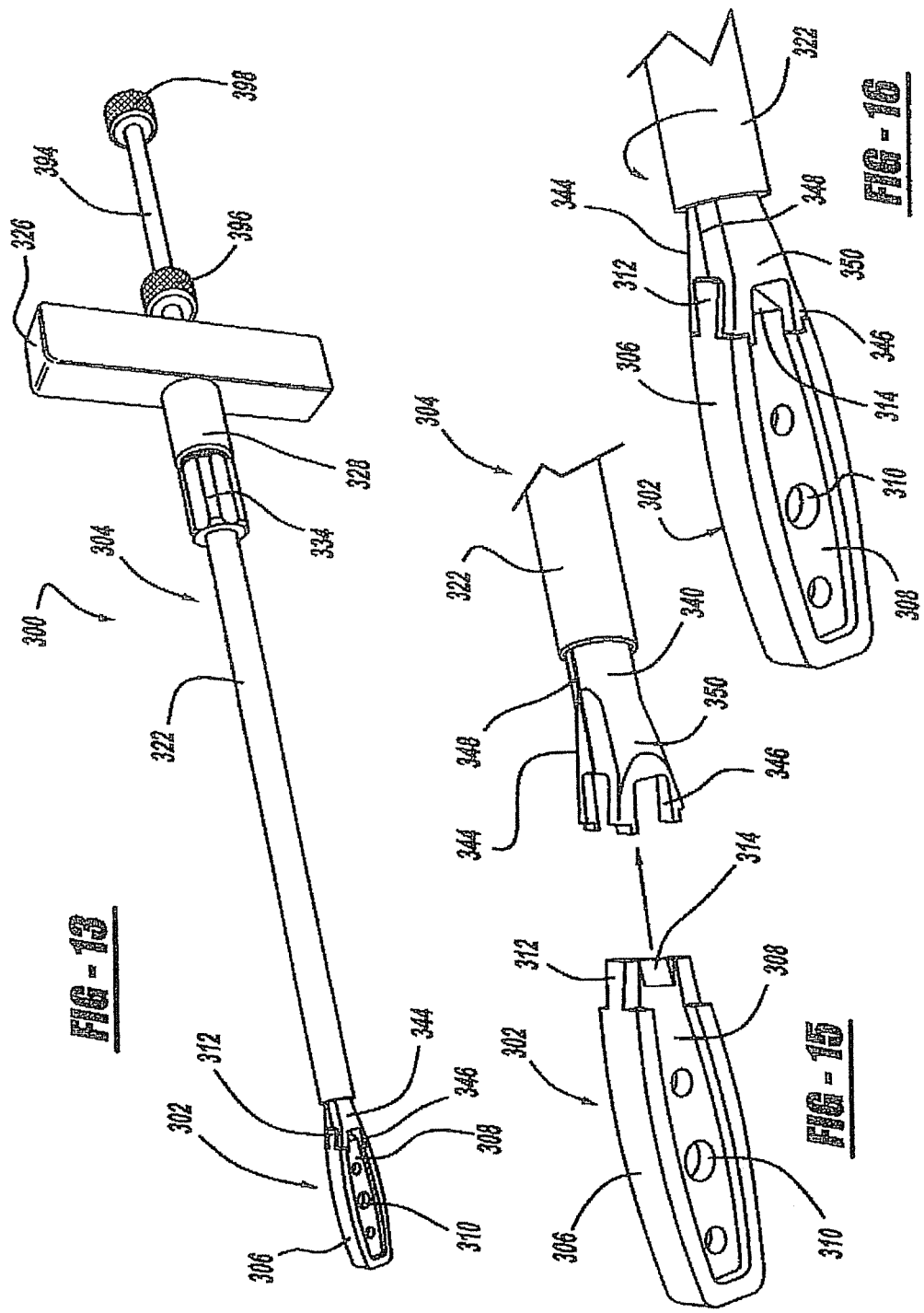

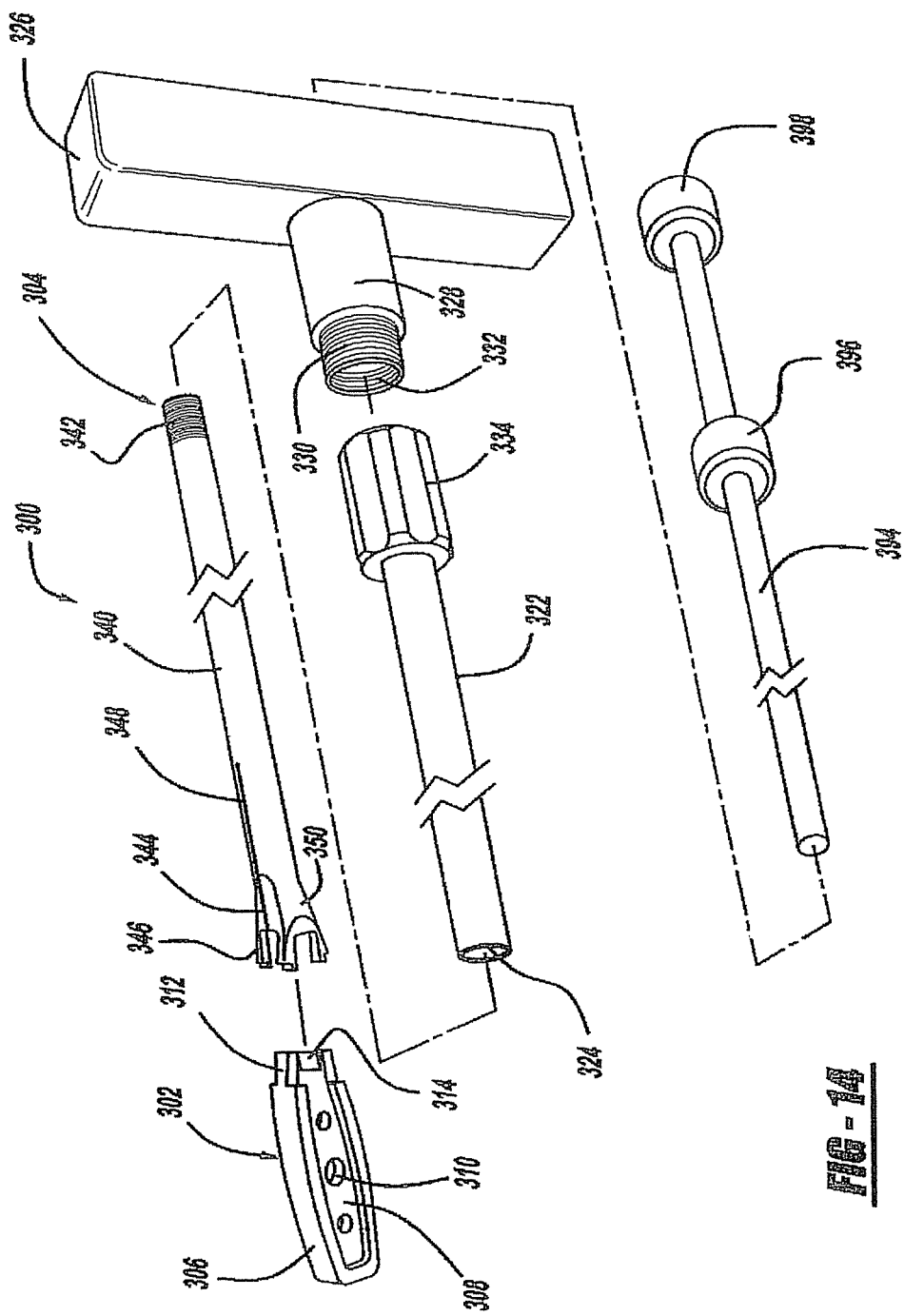

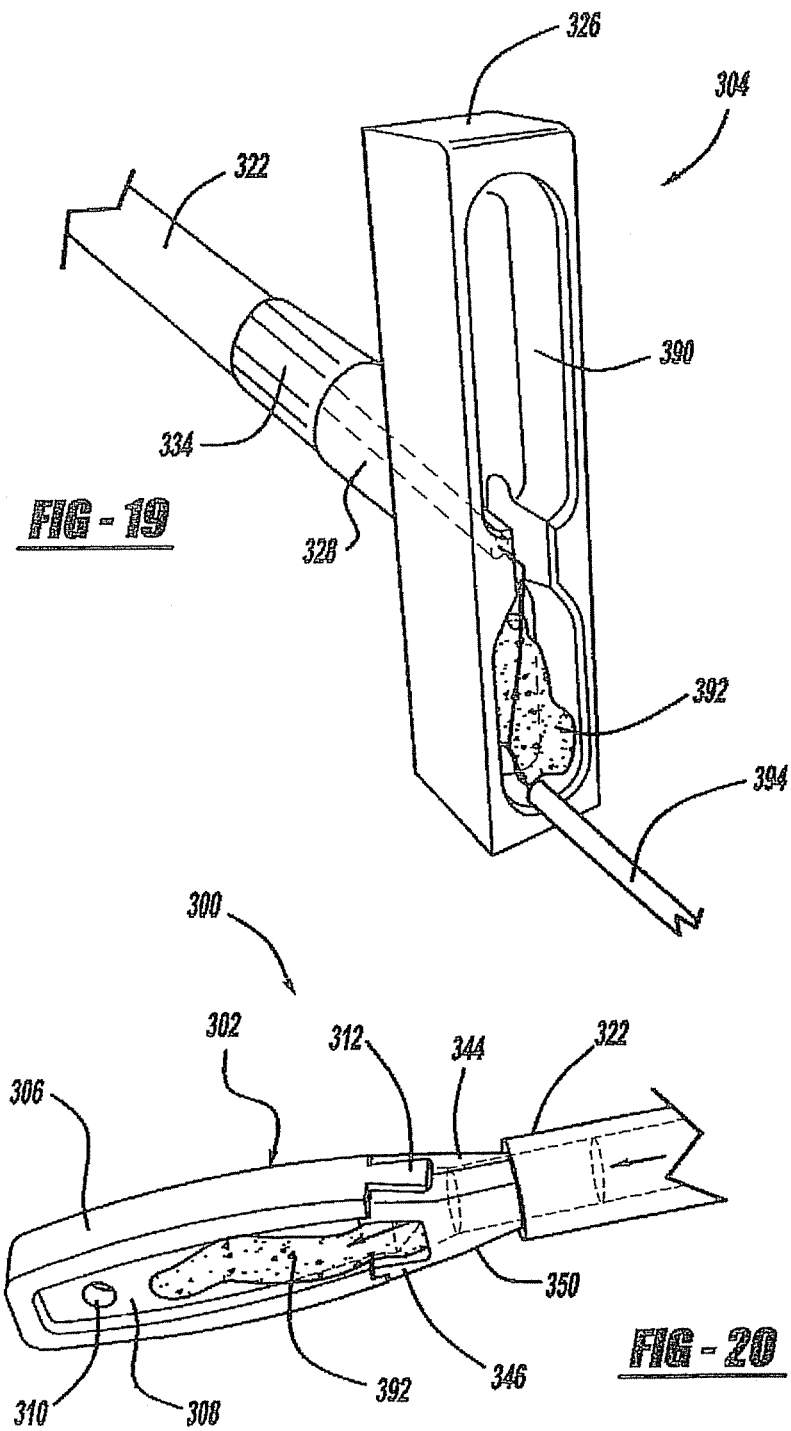

MINIMALLY INVASIVE INTERBODY DEVICE ASSEMBLY

CROSS-REFERENCE TO RELATED APPLICATIONS

The present application is a continuation of U.S. patent application Ser. No. 11/932,175 (U.S. Pat. No. 7,846,210), filed Oct. 31, 2007, titled "Minimally Invasive Interbody Device Assembly," which in turn is a continuation-in-part application of U.S. patent application Ser. No. 11/623,356 (U.S. Pat. No. 7,824,427) filed Jan. 16, 2007, titled "Minimally Invasive Interbody Device," the entire content of which is incorporated herein by reference.

BACKGROUND OF THE INVENTION

1. Field of the Invention

This invention relates generally to an interbody device assembly for inserting an interbody device between two vertebrae during spinal fusion surgery and, more particularly, to a minimally invasive interbody device assembly that includes an interbody device for restoring the disc space height between two adjacent vertebrae during minimally invasive spinal fusion surgery, and an instrument for positioning the device in the disc space and delivering bone graft material to the disc space on both sides of the device.

2. Discussion of the Related Art

The human spine includes a series of vertebrae interconnected by connective tissue referred to as discs that act as a cushion between the vertebrae. The discs allow for movement of the vertebrae so that the back can bend and rotate.

Spinal fusion is a surgical procedure that fuses two or more vertebrae together using bone grafts and/or other devices. Spinal fusion is a commonly performed procedure for the treatment of chronic neck and back pain refractory to non-operative treatments. Spinal fusion is used to stabilize or eliminate motion of vertebrae segments that may be unstable, i.e., move in an abnormal way, that may lead to pain and discomfort. Spinal fusion is typically performed to treat injuries to the vertebrae, degeneration of the spinal discs, abnormal spinal curvature and a weak or unstable spine.

Spinal fusion generally requires a graft material, usually bone material, to fuse the vertebrae together. The bone graft material can be placed over the spine to fuse adjacent vertebrae together. Alternatively, a cage is positioned between the vertebrae being fused, and is filed with the bone graft material. The cage includes holes that allow the vertebrae and the graft material to grow together to provide the fusion. The cage supports the weight of adjacent vertebrae while the fusion is occurring through the holes in the cage. Advantages of an interbody type fusion and cage construct includes the fusion mass is under pressure, which promotes fusion, the disc space height can be restored, which opens the neural foramen and the central canal taking pressure off of the nerves, the alignment of the spine can be restored, and in some cases the graft can be placed with minimal disruption of muscles and ligaments, thus preserving the normal anatomical integrity of the spine.

Typically the bone graft material is autogenous bone material taken from the patient, or allograft bone material harvested from a cadaver. Synthetic bone material can also be used as the graft material. Generally, the patient's own bone material offers the best fusion material and is the current "gold standard." Known bone fusion materials include an iliac crest harvest from the patient, bone graft extenders, such as hydroxyapetite and demineralized bone matrix, and bone morphogenic protein.

In an attempt to preserve normal anatomical structures during spinal surgery, minimally invasive surgical procedures have been devised. One such procedure involves the use of a series of muscle dilators that separate the muscle fibers of the spine to create a pathway to the spine. A Kirschner (K-wire) is initially introduced through a small incision and directed towards the spinal pathology. The position of the K-wire is visualized by a fluoroscopic imaging system to identify its location. An initial narrow diameter muscle dilator is passed over the K-wire, and the K-wire is removed and subsequent larger muscle dilators are continually passed. When the opening is large enough, an access tube or retractor is positioned around the last muscle dilator through which the surgery is performed. The inner sequential muscle dilators are then removed allowing the surgeon to operate through the tubular retractor. The retractors come in a variety of lengths and diameters for different patients and procedures.

As mentioned above, a cage is typically positioned in the interbody region between the vertebrae after the disc has been removed. These cages typically have a box like design. The cage is forced into the interbody region through the surgical area where the bone and disc have been removed. The cage is filled with the bone graft material that subsequently fuses the vertebrae together. However, known cage designs are limited in that they only allow for partial filling of the interbody space where the graft material is maintained within the cage, thus only allowing partial fusion between the vertebrae. Further, the known bone graft cages are difficult to place because of their square or cylindrical shape, and put the nerve roots at risk during the procedure, sometimes resulting in retraction or direct nerve root injury. Also, the known cages do not allow the collapsed disc space height to be fully restored in that they cannot distract the open disc space once they are in place. This can result in the surgeon placing an under-sized cage into the disc space. The cage can move, and thus, migrate into the spinal canal possibly causing nerve injury. Further, the known cage designs require that the bone graft material be placed in the cage prior to it being inserted into the interbody region, which limits the amount of bone material placed in the disc space and subsequent fusion surface. Also, once the cages are placed, they are difficult to remove and reposition. Most cages are not designed specifically to be placed via a minimally invasive approach, which makes them technically difficult to place via a tubular retractor system.

SUMMARY OF THE INVENTION

In accordance with the teachings of the present invention, a minimally invasive interbody device assembly is disclosed that includes an interbody device that restores the disc space height between two vertebrae and an instrument detachably coupled to the interbody device for positioning the device in the disc space and delivering bone graft material to the disc space that is distributed on both sides of the interbody device. The interbody device includes a relatively narrow configuration in one dimension and a relatively wide configuration in an opposite dimension. After the disc space has been cleared, the device is inserted into the disc space using the instrument in a direction so that the wide dimension of the device is substantially parallel to the body of the vertebrae. The device is then rotated by the instrument so that the wide dimension of the device becomes perpendicular to the vertebral body so as to cause the disc space height to be restored. Thus, the device can be placed easily into the disc space without injury to the nerve root. Bone graft material is then forced down the shaft of the instrument so that the bone graft material is distributed on both sides of the interbody device. The instrument is then detached from the device. The bone surrounds the device holding it firmly in place. Additionally, channels within the body of the device allow bone in-growth. More bone can be placed into the disc interspace since its surrounding the device and fills all of the disc space as opposed to a cage design, which contains the bone material.

Additional features of the present invention will become apparent from the following description and appended claims, taken in conjunction with the accompanying drawings.

BRIEF DESCRIPTION OF THE DRAWINGS

FIG. 6 is a perspective view of a fill tube and a minimally invasive interbody device, according to another embodiment of the present invention;

FIG. 7 is broken-away perspective view of a fill tube and a minimally invasive interbody device employing a threaded attachment, according to another embodiment of the present invention;

FIG. 8 is a broken-away perspective view of a fill tube and a minimally invasive interbody device employing a tab and slot connection, according to another embodiment of the present invention;

FIG. 9 is a broken-away perspective view of a fill tube and a minimally invasive interbody device, according to another embodiment of the present invention;

FIG. 9A is an end view of the fill tube shown in FIG. 9;

FIG. 9B is a broken-away end view of the interbody device shown in FIG. 9;

FIG. 13 is a perspective view of a minimally invasive interbody device assembly including an interbody device and an instrument for rotating the device and delivering bone graft material to the disc space, according to another embodiment of the present invention;

FIG. 14 is a blown-apart perspective view of the interbody device assembly;

FIG. 15 is a broken-apart view of the interbody device assembly showing the connection point between the interbody device and the instrument, where the interbody device is detached therefrom;

FIG. 16 is a broken-way perspective view of the interbody device assembly showing the interbody device attached to the instrument;

FIG. 19 is a broken-away perspective view of an end of the instrument of the interbody device assembly showing bone graft material, being delivered down the instrument;

FIG. 20 is a broken-away perspective view of the interbody device assembly showing the bone graft material being distributed around the interbody device.

DETAILED DESCRIPTION OF THE EMBODIMENTS

The following discussion of the embodiments of the invention directed to a minimally invasive interbody device assembly including an interbody device and an instrument for positioning the device and delivering bone graft material to the disc space is merely exemplary in nature, and is in no way intended to limit the invention or its applications or uses.

Figure 1:
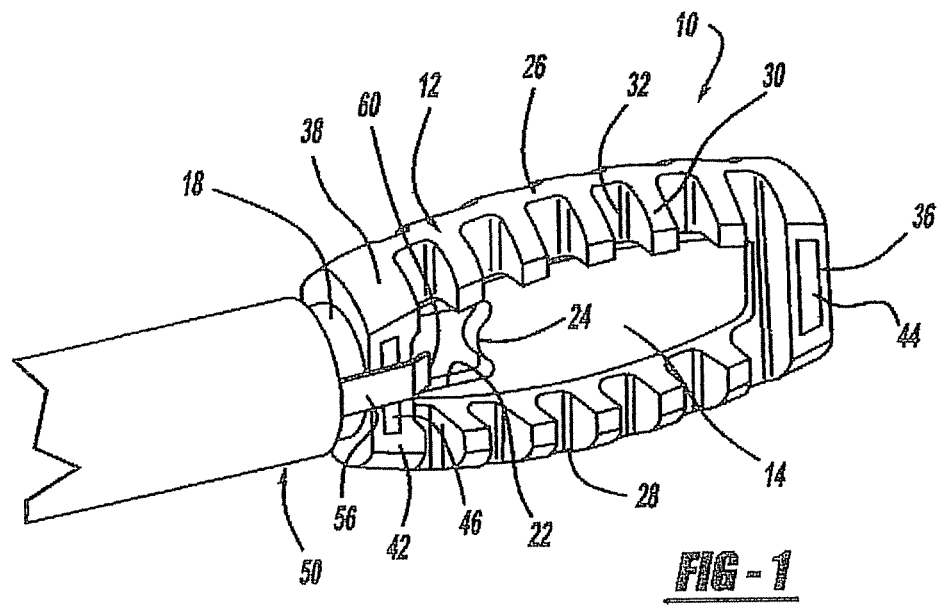
FIG. 1 is a perspective view of a minimally invasive interbody device for restoring the disc space height during spinal fusion surgery, according to an embodiment of the present invention.
Figure 2:
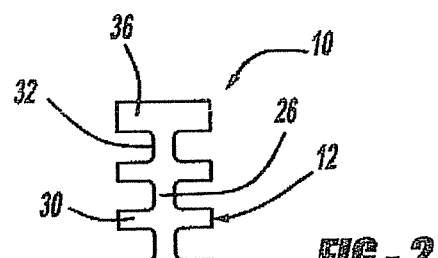
FIG. 2 is a top view of the interbody device shown in FIG. 1.
Figure 3:
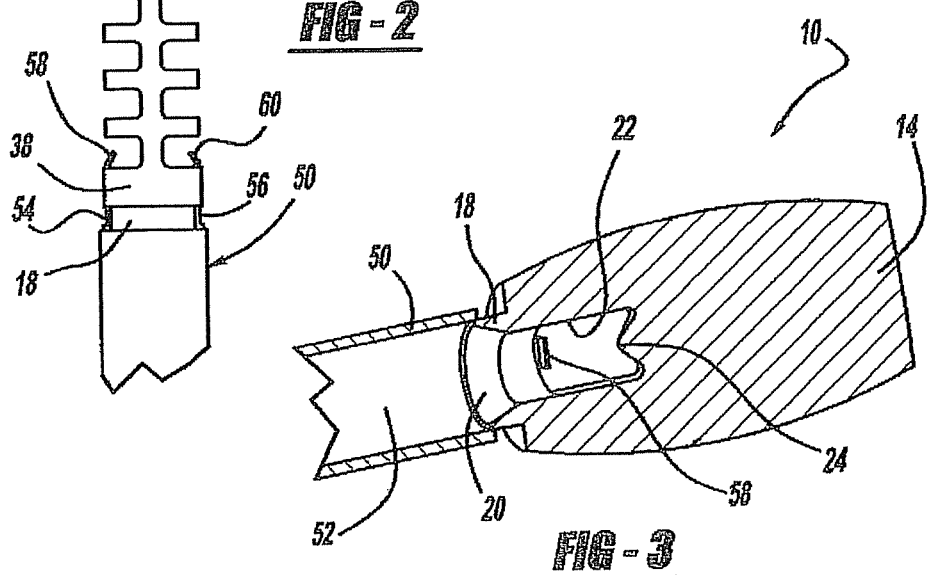
FIG. 3 is a cross-sectional, perspective view of the interbody device shown in FIG. 1.

FIG. 1 is a perspective view, FIG. 2 is a top view and FIG. 3 is a cross-sectional view of a minimally invasive interbody device 10 that is to be positioned within the interbody disc space between two vertebral bodies once the disc has been removed as part of a spinal fusion surgical procedure. As will be discussed in detail below, the device 10 operates to restore the disc space height that has been lost by age or damage and may be causing pain as a result of nerve pinching, as discussed above. Additionally, the device 10 facilitates the distribution of bone graft material within the disc space.

The interbody device 10 includes a perimeter portion 12 and a center plate 14 that are an integral body in this embodiment. The perimeter portion 12 includes opposing spines 26 and 28 having ribs 30 extending therefrom. The ribs 30 define spaces 32 between the ribs 30 along the length of the spines 26 and 28. The perimeter portion 12 also includes a first end piece 36 and a second end piece 38. A coupling tube 18 is formed to the end piece 38 where a bore 20 is defined through the coupling tube 18 and the end piece 38. The center plate 14 includes an opening 22 in communication with the bore 20 to facilitate the distribution of bone graft material. The center plate 14 includes a nub 24 extending into the opening 22, where the nub 24 helps to distribute the bone graft material on either side of the center plate 14 within the disc space. In an alternate embodiment, the center plate 14 can be eliminated. However, some load bearing structure may be needed between the spines 26 and 28.

Although this embodiment includes the spines 26 and 28 and the ribs 30, other embodiments can provide other configurations within the scope of the present invention. For example, the body of the device can be a solid piece having a consistent thickness, where an opening is provided in the body to distribute the bone graft material.

The device 10 can be made of any material suitable for the purposes described herein, such as titanium or a durable plastic. In one embodiment, the device 10 is radiolucent and is invisible on an X-ray. A reflective strip 44 can be attached to the end piece 36 and a reflective strip 46 can be attached to the end piece 38. The reflective strips 44 and 46 can be any suitable opaque marker for the purposes discussed herein. The reflective strips 44 and 46 allow the ends of the device 10 to be visible on an X-ray so that the surgeon will know the position of the device 10 in the disc space.

As discussed above, the bone graft material is introduced through the coupling tube 18. In order to get the bone graft material to the coupling tube 18, a fill tube 50 is attached to the coupling tube 18, as shown. The fill tube 50 includes integral clasps 54 and 56 that extend from an end of the fill tube 50, as shown. The clasps 54 and 56 include angled end portions 58 and 60, respectively, that allow the clasps 54 and 56 to be mounted to the interbody device 10. The interbody device 10 is attached to the fill tube 50 outside of the patient. The fill tube 50 is an elongated member that extends out of the patient's body and allows the surgeon to position the interbody device 10 in the disc space, as will be discussed in more detail below. When the interbody device 10 is attached to the fill tube 50, the clasps 54 and 56 are spread apart and positioned within recesses 42 in the end piece 38, as shown. The clamping force of the clasps 54 and 56 allows the fill tube 50 to be securely attached to the device 10. Also, the angled end portions 58 and 60 are positioned against an opposite side of the end piece 38 to help lock the fill tube 50 the coupling tube 18. The clasps 54 and 56 are robust enough to allow the surgeon to rotate the fill tube 50, and cause the interbody device 10 to rotate within the disc space.

As discussed above, the bone graft material is inserted into the disc space through the coupling tube 18 and the end piece 38. In an alternate embodiment, the bone graft material can be inserted into the disc space through a port outside of the device 10, such as around the end piece 38.

Figure 4:
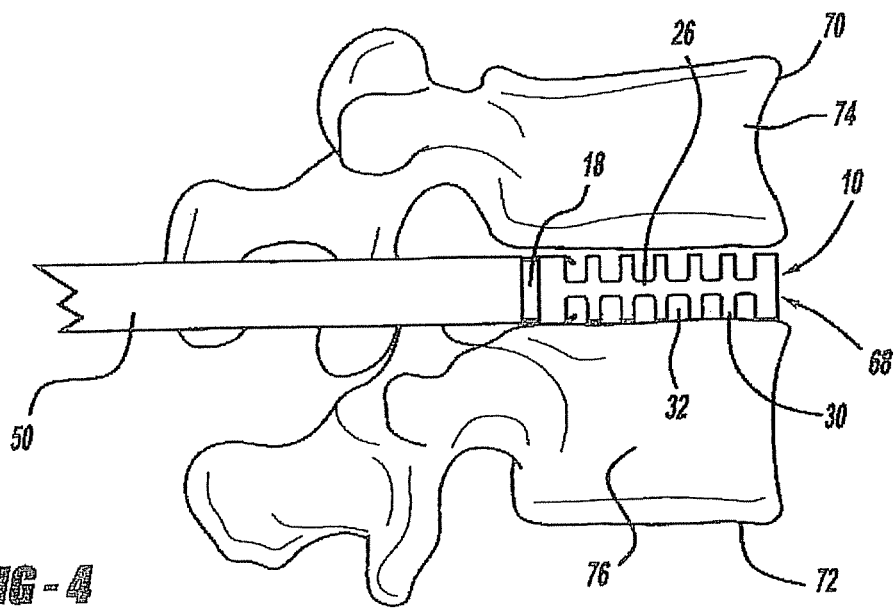
FIG. 4 is a side view of the interbody device shown in FIG. 1 positioned between two vertebrae in an insertion direction.
Figure 5:
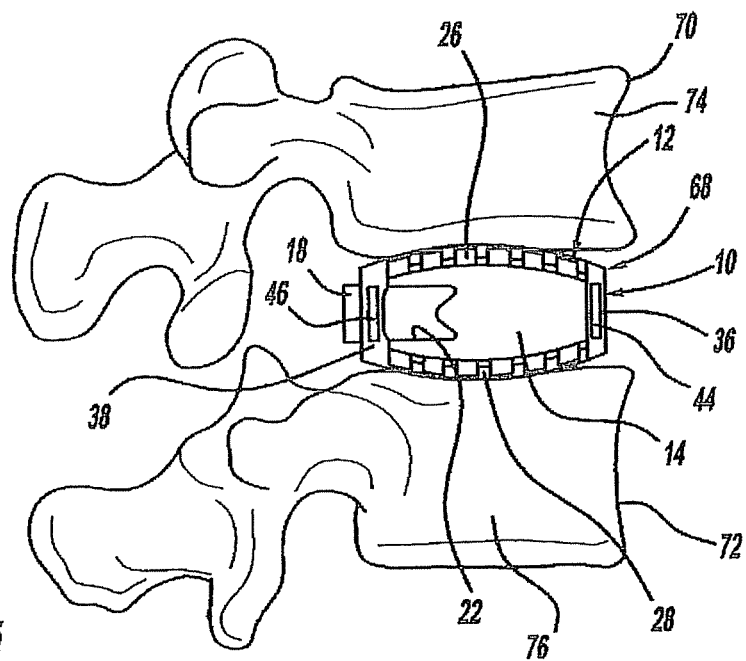
FIG. 5 is a side view of the interbody device shown in FIG. 1 positioned between the vertebrae in a disc height restoring direction.

FIG. 4 shows the interbody device 10 positioned in a disc space 68 between two vertebrae 70 and 72 in an insertion direction where the wider dimension of the device 10 is parallel to the plane of vertebral bodies 74 and 76 of the vertebrae 70 and 72, respectively. Once the interbody device 10 is positioned within the disc space 68, as shown, the fill tube 50 is rotated so that the plane of the center plate 14 becomes perpendicular to the opposing faces of the vertebral bodies 74 and 76, as shown in FIG. 5.

Bone graft material is then introduced through the fill tube 50 into the interbody device 10 through the coupling tube 18 so that it flows into the opening 22 and is spread out on both sides of the center plate 14. The bone graft material will enter the spaces 32 between the ribs 30, and provide a complete and even distribution of bone graft material within the disc space 68 for proper vertebral fusion.

Once the bone graft material has been forced into the disc space, the fill tube 50 is pulled off of the interbody device 10. The clasping strength of the clasps 54 and 56 allow the interbody device 10 to be held to the fill tube 50, but also be removed therefrom under a reasonably low enough force. The interbody device 10 remains in the disc space 68 to maintain the disc space height and facilitate bone fusion.

The spines 26 and 28 and the ribs 30 define the width of the device 10 and the distance between the ribs 26 and 28 defines the height of the device 10. The height of the interbody device 10 is selected to be the desired disc height for a particular disc space so that the disc height is restored by the device 10 as part of the fusion process. The interbody device 10 can be provided in different lengths and heights to accommodate the anatomy of different patients. The width of the device 10 is such that it can be relatively easily slipped into the disc space 68 through a dilator tube (not shown) used in minimally invasive surgical procedures without risk of injury to the nerve roots through the same channel that the disc has been removed from. In one non-limiting embodiment, the device 10 has a width in the range of 3-10 mm and a height in the range of 6-15 mm. The length of the device 10 would be suitable for the size of the disc space, such as 15-25 mm.

FIG. 6 is a broken-away perspective view of a minimally invasive interbody device 80 and associated fill tube handle 82, according to another embodiment of the present invention, where like elements to the device 10 are identified by the same reference numeral. In this embodiment, the coupling tube 18 is replaced with a coupling tube 84. The coupling tube 84 has a tapered portion 86 and a cylindrical portion 88, both having a bore 90 running therethrough. Two elongated opposing tabs 92 and 94 are formed to an outside surface of the cylindrical portion 88. The center plate 14 has been replaced with a series of support columns 96 to provide support when the interbody device 80 is rotated within the disc space. The support columns 96 are intended to represent any suitable load bearing structure within the space defined by the perimeter portion 12.

The fill tube handle 82 includes a fill tube 96 having a central bore 98. A pair of slots 100 and 102 is formed in the bore 98 in alignment with the elongated tabs 92 and 94. The fill tube handle 82 is slipped on to the coupling portion 84 so that the tabs 92 and 94 slide down the slots 100 and 102. The internal bore 98 then forced onto the tapered portion 86 to lock the handle 82 to the interbody device 80. The coupling between the tabs 92 and 94 and the slots 100 and 102 is robust enough so that the interbody device 80 can be rotated within the disc space. Although two of the tabs 92 and 94 are used in this embodiment, it will be appreciated by those skilled in the art that a single tab and slot configuration may be adequate, or more than two tab and slot couplings may be needed. The cylindrical portion 88 is positioned within the bore 98 so that minimal resistance is provided for depositing bone graft material down the bore 98, through the coupling portion 84 and into the space between the ribs 26 and 28.

FIG. 7 is a perspective view of a minimally invasive interbody device 110 and associated fill tube 112, according to another embodiment of the present invention, where like elements to the interbody device 10 are identified by the same reference numeral. In this embodiment, the coupling tube 18 is replaced with a threaded bore 114 that extends through the end piece 38. The fill tube 112 includes a fill tube body 116 having a bore 118 and a threaded end portion 120 at the end of the body 116. The threaded end portion 120 is threaded into the threaded portion 114 in the proper direction to attach and detach the fill tube 112 to the device 110 so that the fill tube 112 can rotate the interbody device 110.

FIG. 8 is a perspective view of a minimally invasive interbody device 130 and associated fill tube 132, according to another embodiment of the present invention, where like elements to the interbody device 10 are identified by the same reference numeral. In this embodiment, the coupling tube 18 is replaced with an internal bore 134 that includes elongated tabs 136 and 138 and slots 140 and 142. The fill tube 132 includes a fill tube body 146 and a narrow diameter end portion 148 defining a shoulder 144 therebetween, where a central bore 150 extends through the fill tube body 146 and the end portion 148. The end portion 148 includes tabs 152 and 154 and slots 156 and 158 that align with the tabs 136 and 138 and the slots 140 and 142 in the bore 134 so as to allow the device 130 to be rotated by the fill tube 132 when the end portion 148 is inserted into the bore 134. Although a specific configuration of tabs and slots are shown between the end portion 148 and the bore 134, any suitable configuration of tab and slots in this manner can be used within the scope of the present invention. The device 130 is held to the fill tube 132 by a friction engagement between the end portion 148 and the bore 134. Alternately, the end portion 148 and the bore 134 can be tapered as a wider diameter to a narrower diameter to provide a better locking arrangement. The shoulder 144 prevents the fill tube 132 from being pushed into the device 130.

FIG. 9 is a perspective view of a minimally invasive interbody device 160 and associated fill tube 162, according to another embodiment of the present invention, where like elements to the device 10 are identified by the same reference numeral. FIG. 9A is an end view of the fill tube 162 and FIG. 9B is a broken-away end view of the device 160. In this embodiment, the coupling tube 18 is replaced with an internal bore 164 that includes a slot 166 and an arced portion 168 defining the ledge 170. The fill tube 162 includes a fill tube body 172 and a narrow diameter end portion 174 defining a shoulder 176 therebetween, where a central bore 178 extends through the fill tube body 162 and the end portion 174. A nub 180 is attached to the end of the end portion 174 and a stop 182 is attached to the end portion 174, as shown. The end portion 174 is inserted into the bore 164 so that the nub 180 aligns with the slot 166. The end portion 174 is slid into the bore 164 so that the nub 180 extends behind the end piece 38. The fill tube 162 is rotated so the nub 180 locks behind the end piece 38. At the same time, the nub 180 rides up a ramp 184 so that the stop 182 is rotated and contacts the ledge 170. The contact between the stop 182 and the ledge 170 allows the device 160 to be rotated within the disc space, as discussed above. The shoulder 176 and the nub 180 lock the fill tube 162 to the device 160. The fill tube 162 can then be rotated in the opposite direction so that the nub 180 again aligns with the slot 166 to remove the fill tube 162, as discussed above.

Figure 10:
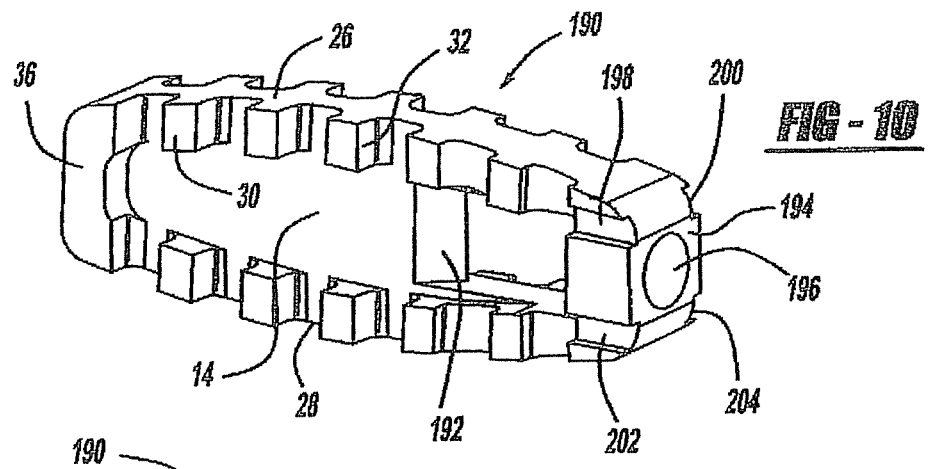
FIG. 10 is a perspective view of a minimally invasive interbody device for restoring the disc space height during spinal fusion surgery, according to another embodiment of the present invention.

FIG. 10 is a perspective view of a minimally invasive interbody device 190 for restoring the disc space height during spinal fusion surgery, according to an embodiment of the present invention, where like elements to the device 10 are identified by the same reference numeral. In this embodiment, the nub 24 is replaced with a triangular ridge 192 that distributes the bone graft material on both sides of the center plate 14. Further, the end piece 38 is replaced with an end piece 194. The end piece 194 includes a cylindrical bore 196 extending therethrough. The end piece 194 also includes a first set of two opposing slots 198 and 200 on opposite sides of the end piece 194 and a second set of two opposing slots 202 and 204 on opposite sides of the end piece 194, as shown.

Figure 11:
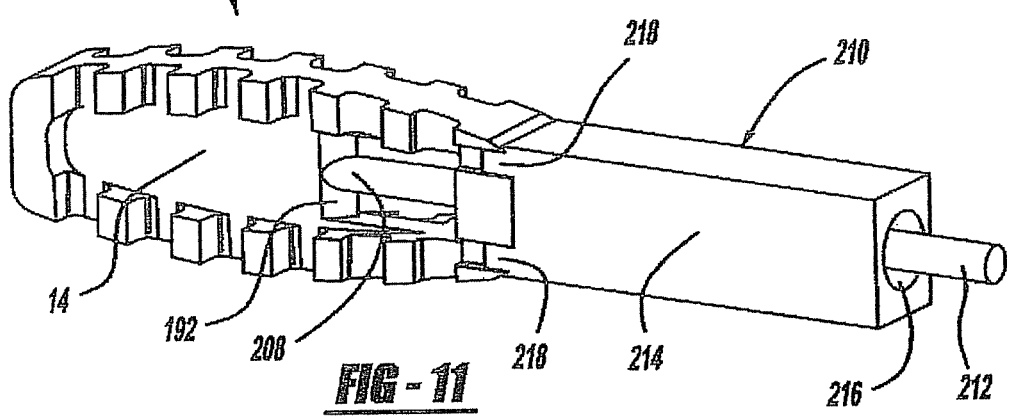
FIG. 11 is a perspective view of the minimally invasive interbody device shown in FIG. 10 and including a rotating tool and a fill tube.

FIG. 11 is a perspective view of the interbody device 190 in combination with a rotating tool 210 and a fill tube 212. The rotating tool 210 includes a rectangular body 214 having a cylindrical bore 216 extending therethrough. The body 214 includes four rigid fingers 218 that are configured to be positioned within the slots 198-204, as shown, to allow the tool 210 to rotate the interbody device 190 for the purposes discussed above. The fill tube 212 extends through the bore 216 and is coupled to or positioned relative to the ridge 190 so that bone graft material forced through the tube 212 is dispersed on both sides of the center plate 14 as discussed above. The end 208 of the fill tube 212 may have a shape that conforms with the shape of the ridge 192.

Figure 12:
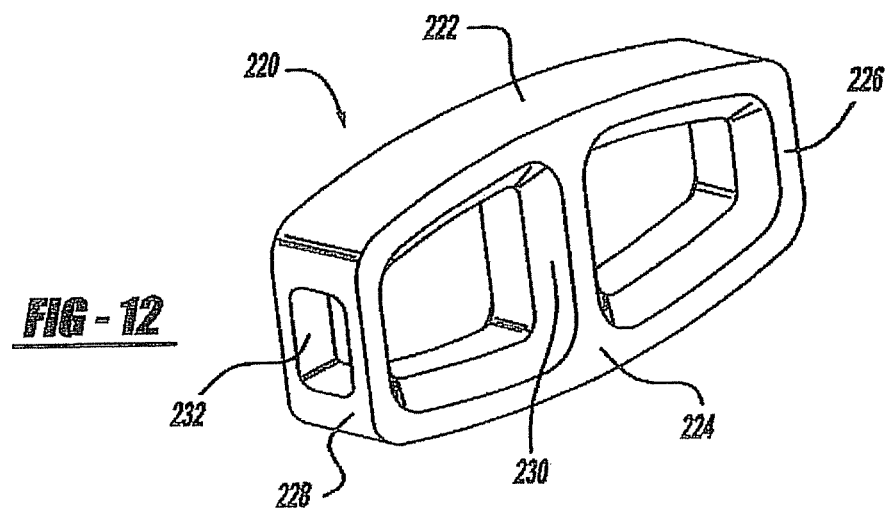
FIG. 12 is a perspective view of a minimally invasive interbody device for restoring the disc space height during spinal fusion surgery, according to an embodiment of the present invention.

FIG. 12 is a perspective view of a minimally invasive interbody device 220 for restoring the disc space height during spinal fusion surgery, according to an embodiment of the present invention. The device 220 includes opposing elongated members 222 and 224 and opposing end pieces 226 and 228 that combine to define a perimeter structure. A center member 230 is coupled to the elongated members 222 and 224 and provides structural support. A rectangular opening 232 is provided through the end piece 228, and accepts a fill tube and rotating tool to rotate the interbody device 220 and provide the bone graft material within the perimeter structure, as discussed above.

FIG. 13 is a perspective view of a minimally invasive interbody device assembly 300 including an interbody device 302 and an instrument 30.4 for positioning the interbody device 302, and delivering bone graft material to the disc space between vertebrae once the interbody device 302 is in the proper position. The interbody device 302 includes a perimeter portion 306 and a center plate 308 defining open chambers on either side of the pate 308. The interbody device 302 includes one or more holes 310 that extend through the plate 308 that allow for better distribution of bone graft material as will become apparent from the discussion below. The interbody device 302 further includes a connecting portion 312 for securing the device 302 to the instrument 304, as will be discussed in greater detail below. The center plate 308 includes a triangular shaped edge 314 that causes bone graft material to be distributed within the open channels on both sides of the plate 308.

The instrument 304 includes a cylindrical body portion 322 having a center bore 324 and a handle 326. The handle 326 includes a securing portion 328 having an outer threaded portion 330 and an inner threaded portion 332. The body portion 322 includes a connection portion 334 having an internal threaded bore that is threaded onto the outer threaded portion 330 to attach the body portion 322 to the handle 326.

The instrument 304 also includes a cylindrical grasping portion 340 having an external threaded portion 342 at one end and a connector portion 344 at an opposite end. The connector portion 344 includes four fingers 346 where two of the fingers 346 are on one side of the connector portion 344 and two of the fingers 346 are on an opposite side of the connector portion 344 where the two sides of the connector portion 344 are separated by a slot 348 that runs a certain distance up the grasping portion 340, as shown. The fingers 346 conform to the shape of the end portion 312 of the interbody device 302 so that the instrument 304 can securely hold the device 302. The grasping portion 340 is inserted into the bore 324 of the body portion 322 so that the threaded end portion 342 threadably engages the internal portion 332 of the holding portion 328 on the handle 326.

To secure the interbody device 302 to the instrument 304, the end portion 312 is inserted into the connector portion 344, and held there. The surgeon will then rotate the body portion 322 using the ribbed grasping portion 334 so that the body portion 322 moves down the grasping portion 340 and contacts a tapered portion 350 of the connector portion 344. The tapered portion 350 causes the slot 348 to close, which pinches the fingers 346 around the end portion 312 rigidly securing the interbody device 302 to the instrument 304. FIG. 15 shows the interbody device 302 relative to the instrument 304, where the body portion 322 is in a detached position, and FIG. 16 shows the interbody device 302 coupled to the connector portion 344 of the instrument 304 where the body portion 322 is in the attached position.

Figure 17:
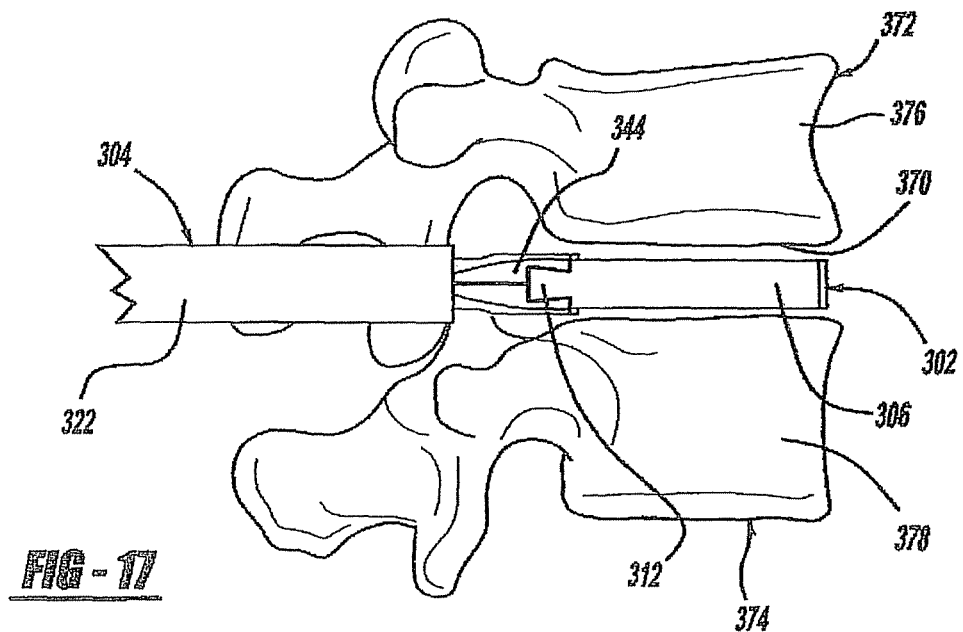
FIG. 17 is a broken-away side view of the interbody device assembly, where the interbody device is positioned between two vertebrae in an insertion direction.
Figure 18:
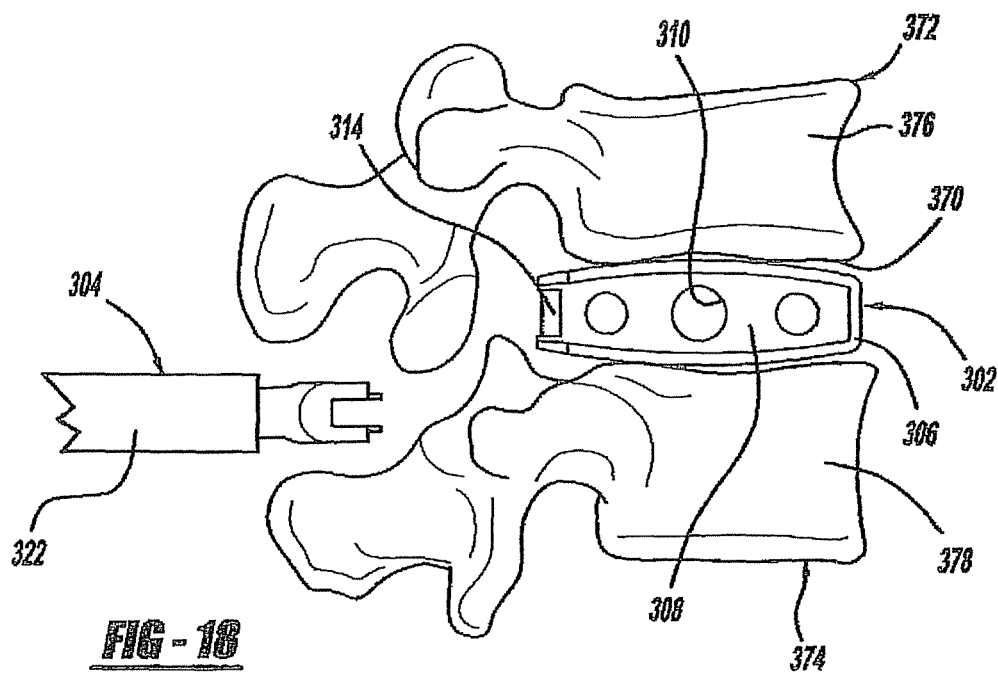
FIG. 18 is a broken-away side view of the interbody device assembly shown in FIG. 13 positioned between the vertebrae in a disc height restoring direction.

When the interbody device 302 is rigidly secured to the instrument 304, the surgeon can then insert the interbody device 302 between the vertebrae in an insertion direction using the instrument 304 using minimally invasive surgical procedures. FIG. 17 shows the interbody device 302 positioned in a disc space 370 between two vertebrae 372 and 374 in an insertion direction where the wider dimension of the device 302 is parallel to the plane of vertebral bodies 376 and 378 of the vertebrae 372 and 374, respectively. Once the interbody device 302 is positioned within the disc space 370, as shown, the instrument 304 is used to rotate the device 302 so that the plane of the plate 308 becomes perpendicular to the opposing faces of the vertebral bodies 376 and 378, as shown in FIG. 18. This restores the disc space height as discussed above.

Once the device 302 is in the proper position, then bone graft material is forced down the bore 324 of the body portion 322 and the bore in the grasping portion 340 through the handle 326. In alternate embodiments, the material can be bone morphogenic proteins or other materials that can restore the normal cells of intervertebral discs, such as stem cells, or promote growth of normal cells within the disc, i.e., normal growth.

FIG. 19 is a broken-away perspective view of an end of the instrument 304 showing a cavity 390 within the handle portion 326. In this non-limiting embodiment, the handle portion 326 is rectangular in shape. However, as will be appreciated by those skilled in the art, other shapes may be equally suitable. The cavity 390 is open to the internal bore extending through the grasping portion 340. Bone graph material 392 is placed in the cavity 390, and then a rod 394, having knurled cylindrical portions 396 and 398, is used to push the bone graft material 392 down the bore in the instrument 304 to the device 302. When the bone graph material hits the edge 314, it is distributed in the chambers on both sides of the plate 308, as shown in FIG. 20. Thus, the bone graft material 392 can fill the disc space on both sides of the device 302 completely to provide the desired final fusion.

Figure 21:
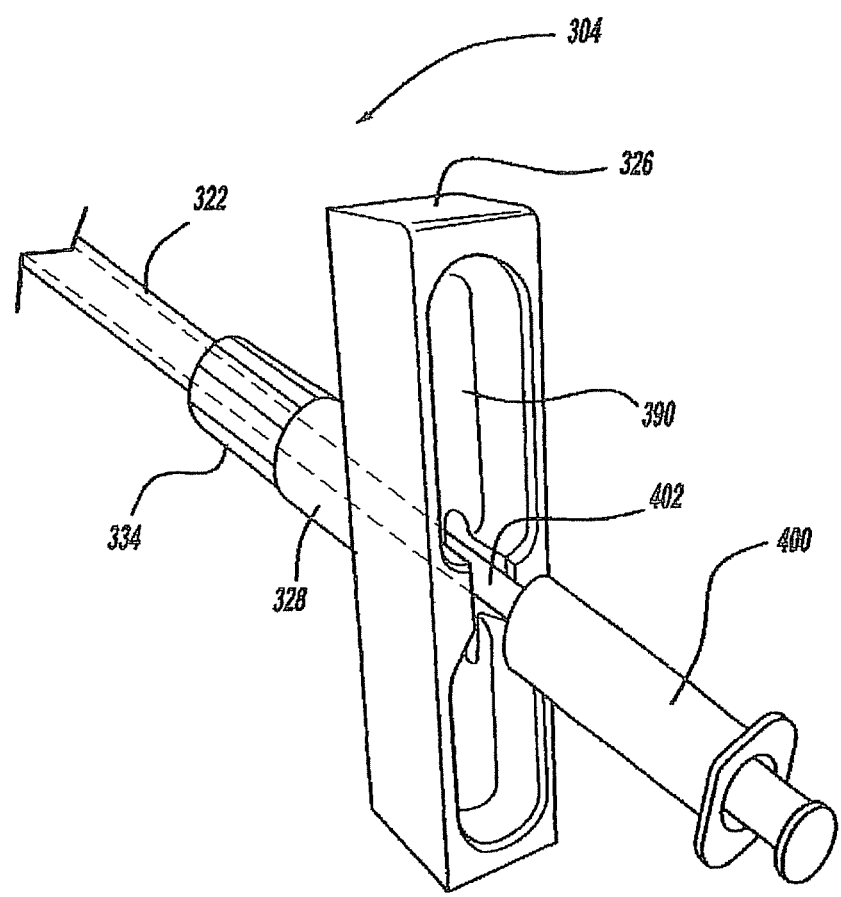
FIG. 21 is a broken-away perspective view of the interbody device assembly employing a syringe for delivering the bone graft material down the instrument, according to another embodiment of the present invention.

The bone graft material 392 can be delivered down the instrument 304 in any suitable manner. In another embodiment, shown in FIG. 21, the bone graph material is delivered through the instrument 304 using a syringe 400 having an extended tubular end portion 402.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. An interbody device assembly for restoring the disc space height of the disc space between opposing vertebral bodies of adjacent vertebrae during a spinal fusion procedure, the assembly comprising:
 a body having a first end, a second end, a top, and a bottom, the body defining a height and a width, the body comprising a distribution feature positioned along a central plane defined by the body, the central plane extending generally from the top to the bottom and from the first end to the second end, the distribution feature configured to distribute bone graft material to either side of the central plane when the top and bottom of the body contact the opposing vertebral bodies;
 an instrument for positioning the interbody device, the instrument including a body portion attached to a handle portion, the body portion including an internal bore, the instrument further including a grasping portion positioned within the bore of the body portion and being connected to the handle portion, the grasping portion having a shape that conforms to a shape on the body so that the instrument is releasably securable to the interbody device; and
 wherein the height of the body is greater than the width of the body, wherein the body is configured to be inserted into the disc space in a substantially flat orientation and to be rotated to an orientation where the top and the bottom contact the opposing vertebral bodies.

2. The interbody device assembly of claim 1 wherein the distribution feature comprises a nub.

3. The interbody device assembly of claim 2 wherein the body comprises a central plate lying along the central plane, and the nub is formed as part of the central plate.

4. The interbody device assembly of claim 1 wherein the distribution feature comprises a ridge.

5. The interbody device assembly of claim 1 further comprising a fill tube, the fill tube configured to be coupled to the body proximate to one of the first and second ends so that bone graft material can be passed through the fill tube to the distribution feature and be distributed to either side of the central plane by the distribution feature.

6. The interbody device assembly of claim 5 wherein the fill tube includes a bore that is substantially open along the length of the bore, wherein the assembly is configured to provide a substantially unimpeded flow path through the bore to the distribution feature when the fill tube is coupled to the interbody device.

7. The interbody device assembly of claim 1, wherein the body portion is threadably attached to the handle portion, and the grasping portion positioned within the bore of the body portion and is threadably connected to the handle portion.

8. An interbody device assembly for restoring the disc space height of the disc space between opposing vertebral bodies of adjacent vertebrae during a spinal fusion procedure, the assembly comprising:
 a body having a first end, a second end, a top, and a bottom, the body defining a height and a width, the body comprising a distribution feature positioned along a central plane defined by the body, the central plane extending generally from the top to the bottom and from the first end to the second end, the distribution feature configured to distribute bone graft material to either side of the central plane when the top and bottom of the body contact the opposing vertebral bodies, the distribution feature comprising a nub; and
 an instrument for positioning the interbody device, the instrument including a body portion attached to a handle portion, the body portion including an internal bore, the instrument further including a grasping portion positioned within the bore of the body portion and being connected to the handle portion, the grasping portion having a shape that conforms to a shape on the body so that the instrument is releasably securable to the interbody device.

9. The interbody device assembly of claim 8 wherein the body comprises a central plate lying along the central plane, and the nub is formed as part of the central plate.

10. The interbody device assembly of claim 8 wherein the distribution feature comprises a ridge.

11. The interbody device assembly of claim 8 further comprising a fill tube, the fill tube configured to be coupled to the body proximate to one of the first and second ends so that bone graft material can be passed through the fill tube to the distribution feature and be distributed to either side of the central plane by the distribution feature.

12. The interbody device assembly of claim 11 wherein the fill tube includes a bore that is substantially open along the length of the bore, wherein the assembly is configured to provide a substantially unimpeded flow path through the bore to the distribution feature when the fill tube is coupled to the interbody device.

13. The interbody device assembly of claim 8, wherein the body portion is threadably attached to the handle portion, and the grasping portion positioned within the bore of the body portion and is threadably connected to the handle portion.

14. An interbody device assembly for restoring the disc space height of the disc space between opposing vertebral bodies of adjacent vertebrae during a spinal fusion procedure, the assembly comprising:
   a body having a first end, a second end, a top, and a bottom, the body defining a height and a width, the body comprising a distribution feature positioned along a central plane defined by the body, the central plane extending generally from the top to the bottom and from the first end to the second end, the distribution feature configured to distribute bone graft material to either side of the central plane when the top and bottom of the body contact the opposing vertebral bodies, wherein the distribution feature comprises a ridge; and
   an instrument for positioning the interbody device, the instrument including a body portion attached to a handle portion, the body portion including an internal bore, the instrument further including a grasping portion positioned within the bore of the body portion and being connected to the handle portion, the grasping portion having a shape that conforms to a shape on the body so that the instrument is releasably securable to the interbody device.

15. The interbody device assembly of claim 14 further comprising a fill tube, the fill tube configured to be coupled to the body proximate to one of the first and second ends so that bone graft material can be passed through the fill tube to the distribution feature and be distributed to either side of the central plane by the distribution feature.

16. The interbody device assembly of claim 15 wherein the fill tube includes a bore that is substantially open along the length of the bore, wherein the assembly is configured to provide a substantially unimpeded flow path through the bore to the distribution feature when the fill tube is coupled to the interbody device.

17. The interbody device assembly of claim 14, wherein the body portion is threadably attached to the handle portion, and the grasping portion positioned within the bore of the body portion and is threadably connected to the handle portion.

18. An interbody device assembly for restoring the disc space height of the disc space between opposing vertebral bodies of adjacent vertebrae during a spinal fusion procedure, the assembly comprising:
   a body having a first end, a second end, a top, and a bottom, the body defining a height and a width, the body comprising a distribution feature positioned along a central plane defined by the body, the central plane extending generally from the top to the bottom and from the first end to the second end, the distribution feature configured to distribute bone graft material to either side of the central plane when the top and bottom of the body contact the opposing vertebral bodies;
   an instrument for positioning the interbody device, the instrument including a body portion attached to a handle portion, the body portion including an internal bore, the instrument further including a grasping portion positioned within the bore of the body portion and being connected to the handle portion, the grasping portion having a shape that conforms to a shape on the body so that the instrument is releasably securable to the interbody device; and
   a fill tube, the fill tube configured to be coupled to the body proximate to one of the first and second ends so that bone graft material can be passed through the fill tube to the distribution feature and be distributed to either side of the central plane by the distribution feature.

19. The interbody device assembly of claim 18 wherein the distribution feature comprises a nub.

20. The interbody device assembly of claim 19 wherein the body comprises a central plate lying along the central plane, and the nub is formed as part of the central plate.

21. The interbody device assembly of claim 18 wherein the distribution feature comprises a ridge.

22. The interbody device assembly of claim 18, wherein the body portion is threadably attached to the handle portion, and the grasping portion positioned within the bore of the body portion and is threadably connected to the handle portion.

* * * * *